(12) United States Patent
Sengun

(10) Patent No.: US 10,383,615 B2
(45) Date of Patent: Aug. 20, 2019

(54) ANCHOR INSERTER

(71) Applicant: MEDOS INTERNATIONAL SARL, Le Locle (CH)

(72) Inventor: Mehmet Ziya Sengun, Canton, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 538 days.

(21) Appl. No.: 14/924,754

(22) Filed: Oct. 28, 2015

(65) Prior Publication Data

US 2016/0045194 A1 Feb. 18, 2016

Related U.S. Application Data

(62) Division of application No. 13/832,777, filed on Mar. 15, 2013, now Pat. No. 9,198,651.

(60) Provisional application No. 61/705,840, filed on Sep. 26, 2012.

(51) Int. Cl.
| A61B 17/04 | (2006.01) |
| A61B 17/88 | (2006.01) |
| A61B 17/00 | (2006.01) |

(52) U.S. Cl.
CPC ...... *A61B 17/0401* (2013.01); *A61B 17/8875* (2013.01); *A61B 2017/00862* (2013.01); *A61B 2017/044* (2013.01); *A61B 2017/0409* (2013.01); *A61B 2017/0448* (2013.01)

(58) Field of Classification Search
CPC ............ A61B 17/8875; A61B 17/7035; A61B 17/7037; A61B 17/0401; A61B 17/1631; A61F 2/0805; A61F 2/0811

USPC ...................... 606/232; 81/64, 450
See application file for complete search history.

(56) References Cited

U.S. PATENT DOCUMENTS

| | | |
|---|---|---|
| 4,030,778 A | 6/1977 | Kaut, Jr. |
| 4,054,306 A | 10/1977 | Sadoff, Jr. |
| 4,071,269 A | 1/1978 | Halling |
| 4,259,992 A | 4/1981 | Kramer |
| 4,377,896 A | 3/1983 | Cox |
| 5,102,276 A | 4/1992 | Gourd |
| 5,145,215 A | 9/1992 | Udell |
| 5,387,016 A | 2/1995 | Joseph |
| 5,611,732 A | 3/1997 | Tirumalai |
| 5,620,352 A | 4/1997 | Tzong |
| 5,791,695 A | 8/1998 | Snider |
| 5,797,918 A * | 8/1998 | McGuire ............... A61B 17/15 606/104 |

(Continued)

FOREIGN PATENT DOCUMENTS

EP 2572651 A1 3/2013

*Primary Examiner* — Diane D Yabut
*Assistant Examiner* — Majid Jamialahmadi

(57) ABSTRACT

An anchor inserter provides for inserting an anchor into a hole in body tissue. The anchor inserter has an elongated shaft with a first axis and a distal end and an insertion tip. The insertion tip has a driving tip extending distally from the distal end of the shaft to terminate in an anchor engaging interface. A resiliency between the anchor engaging interface and the shaft allows bending away from the first axis. An abutment member extends distally from the shaft and has a distally facing abutment surface adjacent the driving tip which abuts the anchor and allows an axial force to be transmitted thereto. Preferably, the abutment member comprises a collar extending from the shaft and coaxially receiving the driving tip.

10 Claims, 2 Drawing Sheets

(56) References Cited

U.S. PATENT DOCUMENTS

| | | | |
|---|---|---|---|
| 5,961,538 A | 10/1999 | Pedlick | |
| 6,527,795 B1 | 3/2003 | Lizardi | |
| 7,063,717 B2 * | 6/2006 | St. Pierre | A61B 17/8875 606/104 |
| 8,449,573 B2 | 5/2013 | Chu | |
| 2003/0132630 A1 | 7/2003 | French | |
| 2007/0017954 A1 | 1/2007 | Dion | |
| 2008/0188854 A1 | 8/2008 | Moser | |
| 2009/0192545 A1 | 7/2009 | Workman | |
| 2010/0049320 A1 | 2/2010 | Lubbers et al. | |
| 2010/0076502 A1 | 3/2010 | Guyer | |
| 2010/0100137 A1 * | 4/2010 | Justis | A61B 17/7037 606/308 |
| 2011/0152867 A1 | 6/2011 | Petrzelka et al. | |
| 2012/0259374 A1 | 10/2012 | Marik | |
| 2013/0079817 A1 * | 3/2013 | Sengun | A61B 17/0401 606/232 |
| 2014/0207233 A1 | 7/2014 | Steiner et al. | |

\* cited by examiner

ANCHOR INSERTER

CROSS REFERENCE TO RELATED APPLICATIONS

This application is a divisional application of U.S. patent application Ser. No. 13/832,777, entitled ANCHOR INSERTER, filed Mar. 15, 2013, which is a non-provisional of U.S. Provisional Application No. 61/705,840, entitled ANCHOR INSERTER, filed Sep. 26, 2012, which is incorporated herein by reference.

BACKGROUND

This application relates to anchor inserters and more particularly to inserters adapted to accommodate insertion of a suture or other anchor off-axis.

Suture anchors provide fixation of suture to bone or other bodily tissue. They are commonly employed to attach soft tissue such as tendons to bone, such as when such soft tissue has been detached from the bone. Suture anchors take many forms but in general are disposed on a distal end of an insertion tool and then implanted into the bone therewith. Typically the anchor is pushed or threaded into a pre-drilled bone hole. Ideally, the axis of the bone hole and the axis of the insertion tool are aligned. If the axis of the insertion tool is oriented off axis it is preferred to have some compliance to allow the anchor to be aligned axially with the bone hole. It can be difficult to provide a compliance that allows sufficient bending off-axis without rupturing, especially when the tool is cannulated to allow suture to pass therethrough.

SUMMARY OF THE INVENTION

The present invention overcomes these and other limitations of the prior art in a simple and elegant design.

An anchor inserter according to the present invention provides for inserting an anchor into a hole in body tissue. The anchor inserter has an elongated shaft with a first axis and a distal end and an insertion tip. The insertion tip has a driving tip extending distally from the distal end of the shaft to terminate in an anchor engaging interface. A resiliency between the anchor engaging interface and the shaft allows bending away from the first axis. An abutment member extends distally from the shaft and has a distally facing abutment surface adjacent the driving tip which abuts the anchor and allows an axial force to be transmitted thereto.

Preferably, the abutment member comprises a collar extending from the shaft and coaxially receiving the driving tip. Preferably, a gap exists between the collar and the driving tip and the driving tip and collar are not interconnected except through their connection to the shaft. The abutment member may thus be more rigid and sturdy for an application of axial force and the driving member more resilient to accommodate the driver shaft (first axis) being moved off of an axis of the insertion tip while the anchor is being inserted, thus allowing proper insertion of the anchor into the hole without applying undue force to the tissue forming the hole.

In one aspect of the invention, the anchor engaging interface comprises a hex driver. Preferably, a tool cannulation extends coaxially from the anchor engaging interface at least to the shaft, such as for example receiving suture from the anchor or for insertion of an anchor over a spinal needle or the like.

In one aspect of the invention, the driving tip extends distally from the shaft about twice as far as the collar extends distally from the shaft.

In one aspect of the invention, an anchor is attached to the insertion tip with the anchor engaging interface of the driving tip received within a complementary tool receiving recess in the anchor and with the abutment surface engaged against a proximally facing surface of the anchor. Such anchor defines an insertion axis and the driving tip has a first configuration wherein the first axis is axially aligned with insertion axis and a second position wherein the driving tip is bent such that the insertion axis is out of alignment with the first axis.

A method according to the present invention provides for inserting an anchor into a hole in bodily tissue. The method comprises the steps of: a) disposing the anchor onto an anchor inserter having a shaft with a first axis and a driving tip extending distally from a distal end of the shaft, the driving tip being engaged to the anchor at an anchor engaging interface of the driving tip; b) applying a distally directed force to the suture anchor via an abutment member adjacent the driving tip and which extends distally from the shaft to abut the anchor, the force urging the anchor into the hole; and c) during at least a portion of the performance of step b), bending the driving tip at a resiliency therealong such that the driving tip bends away from the first axis.

Preferably, structural integrity of the driving tip is maintained in the performance of step c). The driving tip may bend, or perhaps, although not ideally, kink, but will not break into pieces or become detached from the shaft.

In one aspect of the invention, the anchor is rotated via a rotational force imparted through the driving tip while performing step b), such as for example while threading a threaded anchor into tissue.

Preferably, the force applied in step b) is applied through a collar which extends from the shaft and coaxially receives the driving tip. In an aspect of the invention, that portion of the driving tip received within the collar moves relative to the collar during the performance of step c).

In an aspect of the invention, the suture anchor defines an insertion axis which is aligned with the first axis prior to step c) and angles away therefrom during step c).

DETAILED DESCRIPTION

Figure 1:
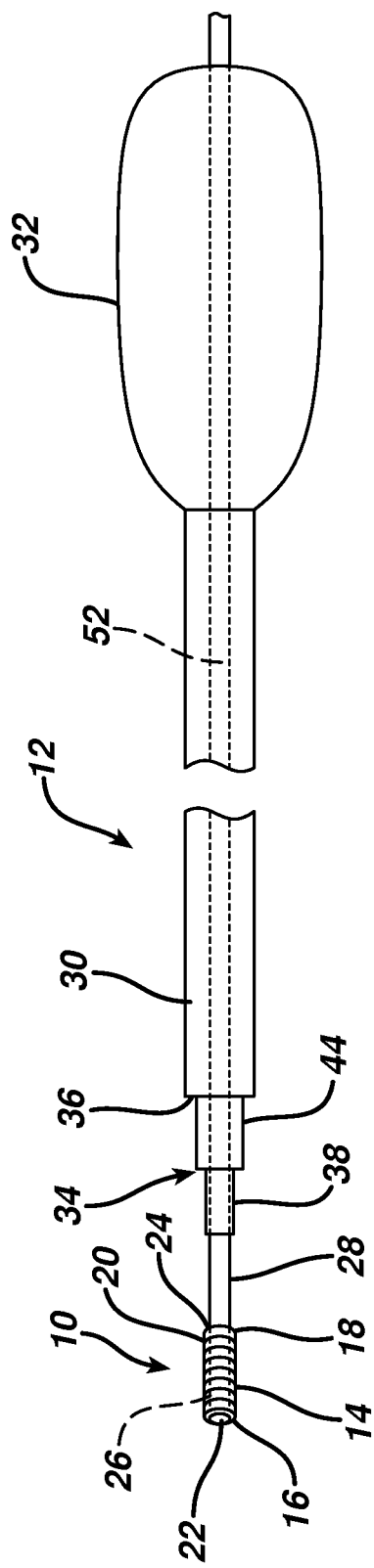
FIG. 1 is an exploded side elevation view of a suture anchor and suture anchor inserter according to the present invention.

FIG. 1 illustrates a suture anchor 10 and suture anchor inserter 12 according to the present invention. The suture anchor 10 comprises an elongated cylindrical body 14 having a distal end 16, proximal end 18, outer threads 20 and a cannulation 22 therethrough wherein at least a proximal portion of the cannulation 22 is hexagonal in shape to form a tool receiving recess 24. The suture anchor 10 is but one example of a suture anchor which may be inserted using the suture anchor inserter 12. A suture bridge 26 spans the cannulation 22 near the distal end 16 and retains a suture 28 passed thereabout. The structure of the suture anchor 10 is illustrative of suture anchors in general, but the invention is not limited to any particular type of suture anchor and the suture anchor inserter 12 according to the present invention has utility with a variety of suture anchor structures as will be appreciated by those of skill in the art.

Figure 2:
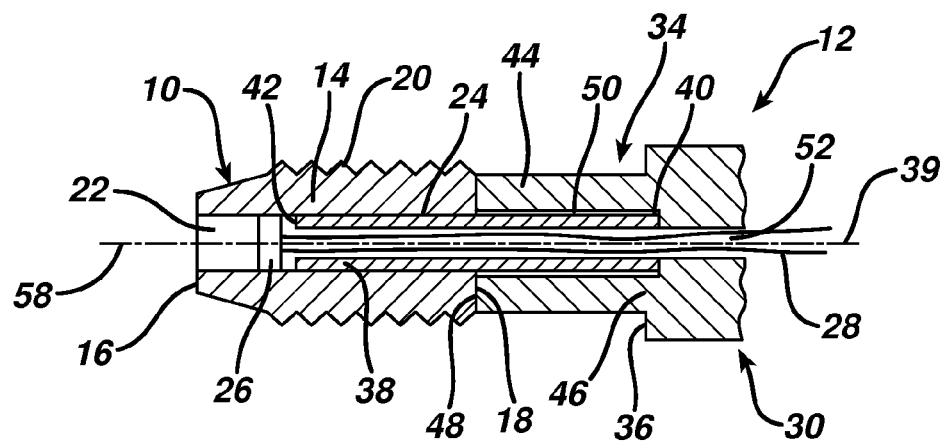
FIG. 2 is a side elevation view in cross-section of the suture anchor of FIG. 1 disposed on a distal end of the suture anchor inserter of FIG. 1.

Turning also now to FIG. 2, the suture anchor inserter 12 comprises an elongated shaft 30 having a proximal handle 32. An insertion tip 34 at a distal end 36 of the shaft comprises an elongated driving tip 38 having an external hexagonal shape adapted to mate with the proximal portion 24 of the suture anchor cannulation 22. An inserter axis 39 extends through the shaft 30 and insertion tip 34. The driving tip 38 is affixed at a proximal end 40 to the shaft distal end 36 and extends out to a distal end 42. A collar 44 also attaches to the shaft distal end 36 at its proximal end 46 and coaxially receives the driving tip 38. The collar 44 extends distally from the shaft distal end 36 about half of the length of the driving tip 38 end terminates in a free distal end 48. An annular gap 50 is provided between the collar 44 and the driving tip 38. A tool cannulation 52 extends through the driving tip 38, shaft 30 and handle 32. In preparation for use, the anchor 10 is inserted onto the insertion tip 34 with the driving tip 38 inserted and mated into the cannulation proximal portion 24 of the suture anchor 10, and with the suture 28 extending proximally from the suture bridge 26 through suture anchor cannulation 22, and the tool cannulation 52. The collar distal end 48 abuts the suture anchor proximal end 18.

The components of the suture anchor inserter 12 can be made from any biocompatible material having desirable strength and other properties, such as a polymer, stainless steel, titanium, or alloys of nickel and titanium. The driving tip 38 in particular might employ materials having strength and resiliency under bending loads with a high breaking strain as for instance 304 annealed stainless steel or superelastic metals such as Nitinol. A weld or proper adhesive should suffice for attaching the driving tip 38 proximal end 40 to the distal end 36 of the shaft 30, but for enhanced strength other arrangements can be made such as insetting the proximal end 40 a certain length into the shaft 30 with a weld or adhesive or compression fit over the extended interface.

Figure 3:
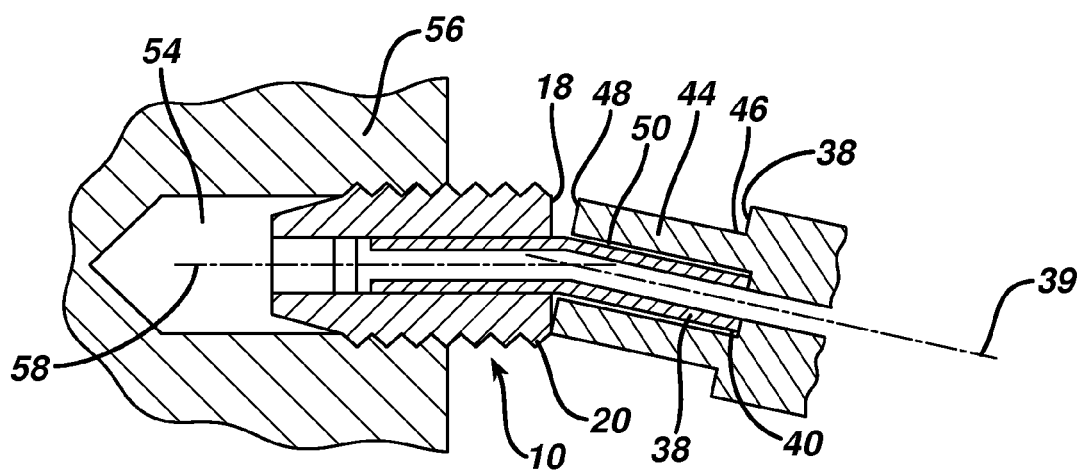
FIG. 3 is a side elevation view of the suture anchor and suture anchor inserter of FIG. 1 with the anchor partially inserted into a bone hole and the suture anchor inserter off-axis from the bone hole and suture anchor.

Turning also now to FIG. 3, the suture anchor 10 is shown being inserted into a hole 54 in a bone 56. The hole has an axis 58 and the shaft has an axis 39 which is angled with respect to the hole axis 58. In a typical prior driver the driving tip 38 would not have an extended length passing through the collar 44, but would rather extend simply from the shaft 30 the same distance as it extends past the collar 40 in the current invention, putting a stress riser at its interface with the shaft. The present design allows the driving tip 38 to be extended in length while still having a proper abutment against the anchor proximal end 18 via the collar distal end 48. The gap 50 is preferably small, just allowing sliding between the driving tip 38 and the collar 40, but could be expanded to allow enhanced bending of the driving tip 38 over its length.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. An anchor inserter for inserting an anchor into a hole in body tissue, the anchor inserter comprising an elongated shaft having a first axis and a distal end; and
   an insertion tip, the insertion tip comprising:
      a driving tip extending distally from the distal end of the shaft to terminate in an anchor engaging interface
      an abutment member extending distally from the shaft and having a distally facing abutment surface adjacent the driving tip whereby to abut an anchor and allow an axial force to be transmitted thereto; and
      a resiliency in the driving tip which allows bending away from the first axis at a location distal of the abutment member.

2. An anchor inserter according to claim 1 wherein the abutment member comprises a collar extending from the shaft and coaxially receiving the driving tip.

3. An anchor inserter according to claim 2 and further comprising a co-axial gap between the collar and the driving tip.

4. An anchor inserter according to claim 3 wherein the gap is annular and wherein the resiliency is such that the driving tip can be bent away from the first axis to close at least a portion of the gap and contact the collar without the driving tip breaking.

5. An anchor inserter according to claim 2 wherein the driving tip and collar are not interconnected except through their connection to the shaft.

6. An anchor inserter according to claim 2 wherein the driving tip extends distally from the shaft about twice as far as the collar extends distally from the shaft.

7. An anchor inserter according to claim 1 wherein the anchor engaging interface comprises a hex driver.

8. An anchor inserter according to claim 1 and further comprising a tool cannulation extending coaxially from the anchor engaging interface at least to the shaft.

9. An anchor inserter according to claim 1 and further comprising an anchor attached to the insertion tip with the anchor engaging interface of the driving tip received within a complementary tool receiving recess in the anchor and with the abutment surface engaged against a proximally facing surface of the anchor.

10. An anchor inserter according to claim 9 wherein the anchor defines an insertion axis and the driving tip has a first configuration wherein the first axis is axially aligned with insertion axis and a second position wherein the driving tip is bent such that the insertion axis is out of alignment with the first axis.

* * * * *